(12) United States Patent
Trava

(10) Patent No.: US 9,168,778 B2
(45) Date of Patent: Oct. 27, 2015

(54) DENTAL-BASED IDENTIFICATION SYSTEM

(76) Inventor: Brian P. Trava, Hawthorne, NJ (US)

( * ) Notice: Subject to any disclaimer, the term of this patent is extended or adjusted under 35 U.S.C. 154(b) by 498 days.

(21) Appl. No.: 13/557,496

(22) Filed: Jul. 25, 2012

(65) Prior Publication Data

US 2014/0028010 A1 Jan. 30, 2014

(51) Int. Cl.
| | |
|---|---|
| G05B 19/00 | (2006.01) |
| H04Q 5/22 | (2006.01) |
| A61C 11/00 | (2006.01) |
| A61C 5/08 | (2006.01) |
| A61C 13/08 | (2006.01) |
| G06Q 50/00 | (2012.01) |
| G06K 9/00 | (2006.01) |
| B42D 15/00 | (2006.01) |

(52) U.S. Cl.
CPC .................................... B42D 15/00 (2013.01)

(58) Field of Classification Search
CPC ............ G06K 9/00; G06K 9/22; G06K 7/01; G06Q 50/00
See application file for complete search history.

(56) References Cited

U.S. PATENT DOCUMENTS

| | | | | |
|---|---|---|---|---|
| 7,742,547 | B2 * | 6/2010 | Lin et al. | 375/341 |
| 2004/0125988 | A1 * | 7/2004 | Coetzee et al. | 382/112 |
| 2007/0093234 | A1 * | 4/2007 | Willis et al. | 455/410 |
| 2007/0102635 | A1 * | 5/2007 | Ma et al. | 250/338.1 |
| 2007/0183633 | A1 * | 8/2007 | Hoffmann | 382/116 |
| 2008/0172386 | A1 * | 7/2008 | Ammar et al. | 707/6 |
| 2011/0140856 | A1 * | 6/2011 | Downie et al. | 340/10.1 |
| 2012/0126948 | A1 * | 5/2012 | Brunski | 340/10.1 |

* cited by examiner

*Primary Examiner* — Jennifer Mehmood
*Assistant Examiner* — Pameshanand Mahase
(74) *Attorney, Agent, or Firm* — Myers Wolin, LLC

(57) ABSTRACT

A dental-based identification system for identification of individuals comprises a database configured to maintain a record of each individual registered in the system, wherein each record includes at least an identification (ID) number included in a dental-based identification tag and identification information of the individual, wherein the ID number uniquely identifies the individual; and an identification server configured to receive a radiograph of at least one tooth to which the dental-based identification tag is bonded, to detect the ID number included in the dental-based identification tag, and to search a recording associated with the detected ID number, wherein the identification server is further configured to generate and send a message upon identification of the individual.

20 Claims, 3 Drawing Sheets

DENTAL-BASED IDENTIFICATION SYSTEM

TECHNICAL FIELD

This invention generally relates to identification tags and system, and more particularly a dental-based identification system and tag for identifying missing individuals including children.

BACKGROUND

In a many situations it is required to obtain information about the identity of individual for identification purposes. For example, forensic investigations usually need to identify the individual who committed a crime or the victim of the crime. The body or remains of the victim in some cases does not allow for easy identification of the individual. Similarly, in the military, identification of dead and wounded military personnel is also needed.

Forensic science uses a number of methods for identification purposes. An example for such a method includes collection and analysis of crime scene DNA samples and comparing the DNA characteristics of the sample against a DNA sample from a known person. Another identification method includes collecting biometric data (fingerprint) at the crime scene and comparing the collected data to a biometric database that contains already collected fingerprints.

Biometric information can be somewhat effective in tracing the criminal, but it may not be effective in identifying the victim in a situation where no friction ridges remain. The DNA samples may be more robust in this sense, but complex procedures, performed by expert, are required to analyze the DNA samples to obtain details of the potential source of that sample. Thus, it may take a few days until the identification is completed. Further, in both cases, known samples of either biometric or DNA are needed to identify the individual. Thus, as currently there is not a central repository that contains DNA and/or biometric data, these methods of identification may not be practical.

Another simple identification means is an identification tag typically worn by military personnel. This type of tag is usually fabricated from a corrosion-resistant metal or alloy, such as aluminum or stainless-steel, where the individual information is embossed thereon. However, this type of identification tag can be utilized to identify the individual only as long as the tag is attached to the body.

Dental records can also be used for human identification from skeletal remains. However, the dental records of individuals can be used only if such records have been gathered and saved by the individual's dentists. Further, as currently there is no central registry of dental records, there should first be a reasonably accurate sense who the individual is, in order to allow proper identification. That is, an identification process using dental records typically includes examining the skeletal remains to get an idea of age, sex, race, and so on. This information is then checked against a database of missing people, open murder cases, open accident cases, and so on. Once the investigators have a general idea who the body may be, dental records are used to sort among a smaller number of possibilities. Thus, such an identification process may take a long time and in some case may not be practical, as a central repository of all dental records is currently not available.

Therefore, it would be advantageous to provide an efficient and practical individual identification solution for at least the purpose of tracing people and forensic investigations thereof.

BRIEF DESCRIPTION OF THE DRAWINGS

Various embodiments are particularly pointed out and distinctly claimed in the claims at the conclusion of the specification. The foregoing and other objects, features, and advantages of the invention will be apparent from the following detailed description taken in conjunction with the accompanying drawings.

DETAILED DESCRIPTION

Figure 1:
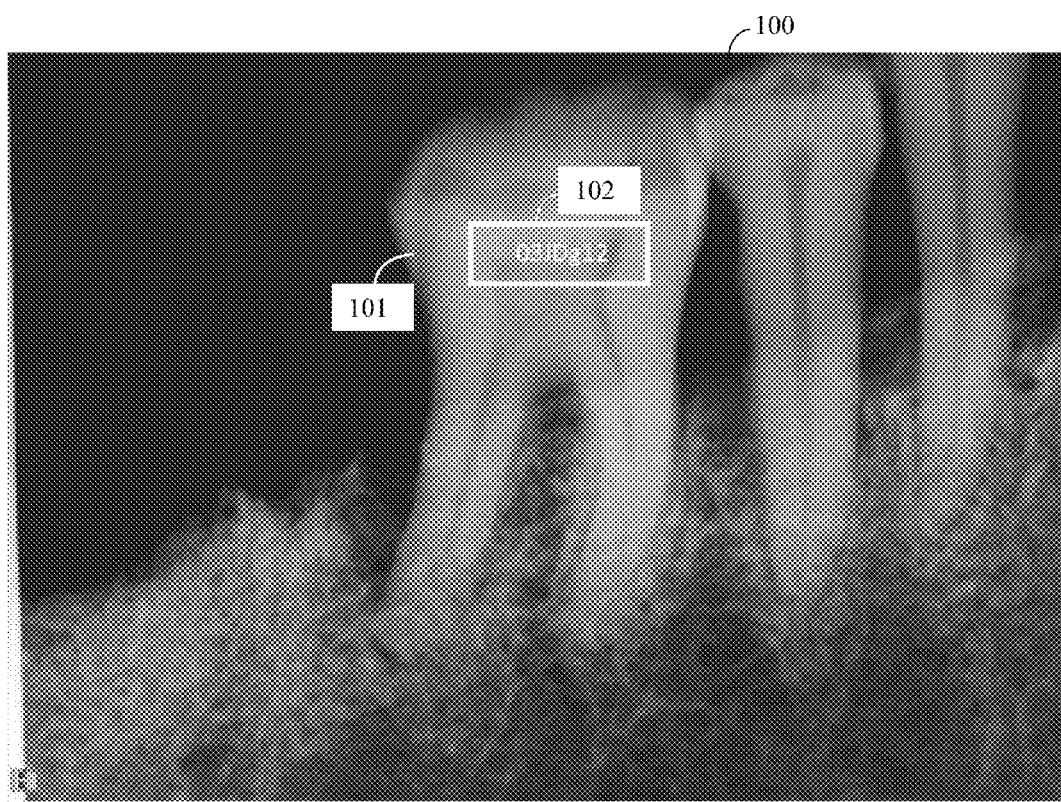
FIG. 1 is a diagram illustrating an exemplary radiograph of a tooth including the dental-based identification tag designed according to one embodiment.

The embodiments disclosed herein are only examples of the many possible advantageous uses and implementations of the innovative teachings presented herein. In general, statements made in the specification of the present application do not necessarily limit any of the various claimed inventions. Moreover, some statements may apply to some inventive features but not to others. In general, unless otherwise indicated, singular elements may be in plural and vice versa with no loss of generality. In the drawings, like numerals refer to like parts through several views.

In an embodiment disclosed, a dental-based identification tag is utilized to identify an individual. The dental-based identification tag can be realized as a sticker bonded on the back of the tooth using a bonding agent. The sticker can be made of a clear plastic material. The bonding agent may be any material known in the related that adheres and protects an object to a tooth. For example, the bonding agent may be curable liquid plastic resin provided by Caulk Prime & Bond NT, and the like. In an embodiment, the bonding process includes, acid etching the tooth, bonding the sticker to the back of the tooth using a bonding agent (e.g., curable liquid plastic resin) to attach the sticker to the patient's tooth, then placing a light cured composite resin, compatible with the bonding agent to protect the tag (sticker). In another embodiment, the sticker can be placed in a dental crown in a lab processed crown. The dental crown is typically bonded to a tooth using dental cement. The procedure of bonding the sticker to the tooth can be performed by a dentist or hygienist.

On the sticker an identification (ID) number unique to the individual is printed using radio-opaque ink. The radio-opaque ink is visible through a radiograph. Thus, when an X-ray image of the tooth including the tag is taken, the printed ID number is revealed. In FIG. 1 an exemplary image is shown of a radiograph 100 of a tooth 101 with the dental-based identification tag 102. The ID number printed on the tag is 'O3JDg12'. It should be appreciated that the materials used in the disclosed identification tag, bonding agent, and radio-opaque ink do not induce any artificial feeling in the individual's mouth.

The ID number may be a combination of characters uniquely identifying the individual. In one embodiment, the ID number is selected from a centralized database, ensuring that the same ID number will not be assigned to two or more different persons. In another embodiment, the tag may be in a form of a micro-chip designed to carry information uniquely identifying the individual.

Figure 2:
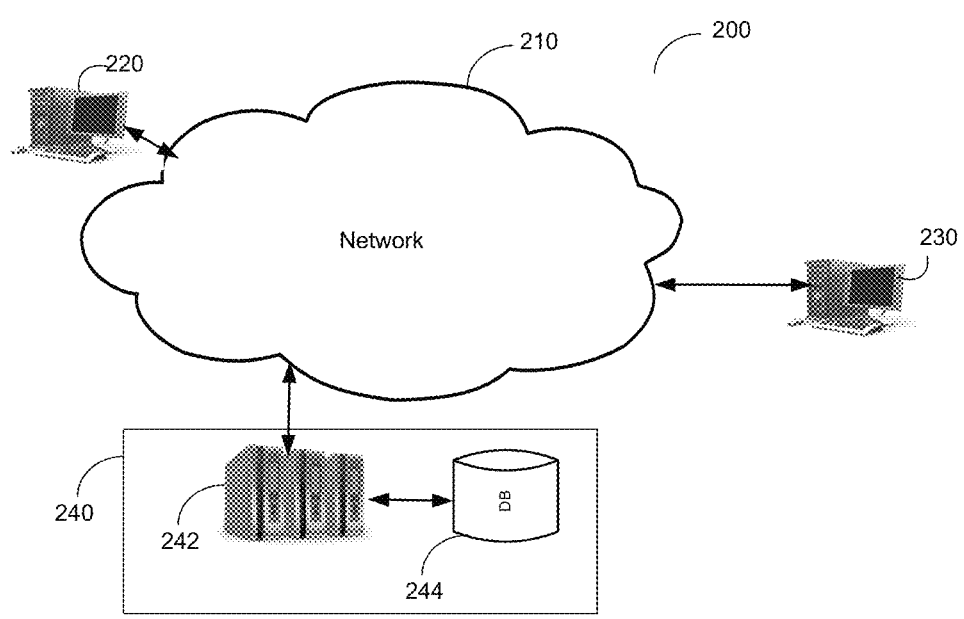
FIG. 2 is a diagram of a network system utilized to describe the dental-based identification system according to one embodiment.

FIG. 2 shows an exemplary and non-limiting diagram of a network system 200 utilized to describe the dental-based identification system according to one embodiment of the invention. As depicted in FIG. 2, to a network 210 there are connected clients 220 and 230 that communicate with an identification system 240 through the network 210. The network 210 may be, but is not limited to, any type of a local area network (LAN), a wide area network (WAN), a metropolitan area network (MAN), or any combination thereof.

Each of clients 220 and 230 may be configured to upload information to or retrieve information from the identification system 240. The user of each of clients 220 and 230 may be a dentist, an investigator, or any person authorized to access the information contained in the identification system 240. For the sake of the simplicity of the description and without limiting the scope of the invention, the authorized user, e.g., a dentist, as client 220, enters information to the system 240, while the authorized user of the client 230 retrieves information from the system 240.

The identification system 240 includes an identification server 242 and a database 244, which may be in any form of tangible data repository 244. The database 244 may be directly connected to the server 242 through a secured connection or through the network 210 (not shown in FIG. 2). In a different configuration, the database 244 is part of the server 242. The server 242 includes at least a processing unit and a tangible memory (not shown). The memory includes at least instructions that when executed by the processing unit cause the execution of the identification processes described herein.

Through the client 220 the authorized user registers the ID number printed on the identification tag. As part of the registration process, an X-ray image of the tag (prior to bonding) is taken to confirm the ID number printed therein. Further, an X-ray of the tooth with the identification tag can also be taken and recorded in the database 244 to be later used as a reference. In addition, identification information of the individual is recorded together with the ID number included in the tag. The identification information includes, but is not limited to, name, age, gender, medical information (e.g., existing medical conditions, blood type), eye colors, height, contact information in case of emergency, and so on. The registration may be performed by the dentist after implanting the dental-base identification tag. In another embodiment, an authorized user (e.g., a parent or guardian) enters information about the individual and only the authorized user will have access to the stored information. In this embodiment, the dentist sends the X-ray with the tooth. The information is saved in the database 244 in an entry associated with the ID number of the tag. The information recorded in the database 244 may be updated by an authorized user.

It should be noted that the recorded information may also be distributed among a plurality of databases. It should be further noted that different permissions may be assigned to different authorized users of the database 244 or the distributed databases.

The identification information stored in the database 244 may be utilized for fast and easy identification of an individual using only a radiograph showing at least the tooth to which the identification tag is bonded. Specifically, in order to identify an individual whose identification information is recorded in the database 244, a radiograph (e.g., radiograph 200) of the tooth showing the ID number is uploaded to the server 242, for example, through the client 230. The client 230 may be connected to an X-ray camera (not shown in FIG. 2).

The server 242 processes the uploaded radiograph image to discover the ID number printed in the dental-based identification tag (e.g., tag 102 of FIG. 1). This can be performed using image processing techniques known to one of ordinary skill. Alternatively, the ID number appearing on the radiograph can be entered by an authorized user through client 230 and provided as an input to the server 242.

The identification server 242 searches the database 244 for an entry associated with the input ID number to retrieve the identification information saved in the respective entry. The identification server 242 returns the retrieved information to the client 230. In a certain embodiment, the server 242 can also process the retrieved information to determine if further actions are required, and performs such actions as needed. For example, the server 242, based on a pre-determined set of instructions in the respective entry, can notify enforcement authorities, the guardians, and so on, that an individual has been identified. The server 242 may also detect the location from which the ID number (or the radiograph) was provided, e.g., the location of the client 230, and include the location also in the notification. The notification can be sent as an email address, a text address, a voice message, and the like, or combination thereof. Thus, the identification system 240 can identify an individual within seconds of the moment the radiograph/ID number associated with the dental-based identification tag has been uploaded to the server 242.

It should be appreciated that the identification system 240 disclosed herein, can be utilized to identify and trace missing persons either live or dead using the radiograph of a tooth containing the identification tag. Thus, the system 240 can be efficiently utilized in forensic investigations, in the military for identification of military personal, and so on.

In a non-limiting embodiment, the identification system 240 can be used to identify and trace an abducted child in a matter of seconds no matter how long the child has been missing. Specifically, when a child visits a dentist for a treatment, the dentist takes an X-ray of the child's teeth. If the dental-based identification tag was bonded to one of the child's teeth, then the ID number printed therein will be visible.

The dentist may then upload the X-ray image (i.e., radiograph) to the server 242 through, for example, the client 230. Thereafter, the server 242 processes the uploaded X-ray image to detect an entry in the database 244 corresponding to the ID number of the child as appears in the image. If such an entry is found, the child's name (or any identification details recorded in the respective entry including, but not limited to, the ID number) are compared against a file of missing people, to determine if the child is missing. This file may be maintained in the database 244 or held in a different database connected to the network 210 to which the server 242 has a connection. If it is determined that a child's identification information is included in the missing persons file, the server 242 generates a notification alert indicating that the missing child has been located. Such an alert can be sent to the dentist's office and/or to enforcement authorities. As mentioned above, the notification alert may include full identification information about the child as stored in the database 244 together the location of the dentist from where the X-ray image was uploaded. In an embodiment, the location can be detected based on the internet protocol (IP) address of the client 230. Alternatively or collectively, the location of each authorized user (including, but not limited to, dentists) can be saved in the database 244. Thus, the location of the dentist who uploaded the radiograph can also be retrieved from the database 244 and included in the notification alert sent to the enforcement authorities.

The identification system 240 can also be beneficial in identifying an individual from skeletal remains. Accordingly, an X-ray image of the jaw bone is taken. If one of the teeth in the remains includes the dental-based identification, then the ID number printed therein will be visible. An authorized user (e.g., a forensic investigator) may then upload the X-ray image (i.e., radiograph) to the server 242 through, for example, the client 230. Thereafter, as described above, the server 242 processes the uploaded X-ray image to detect an entry in the database 244 corresponding to the ID number that appears in the image. If a corresponding entry is found in the database 244, then identification information is retrieved and presented to the authorized user.

An X-ray image of the jaw bone can also be uploaded to the identification server 242 for identification of dead or wounded soldiers. For wounded soldiers, medical information of the indentified individual can be retrieved and presented to an authorized user (e.g., a physician).

Figure 3:
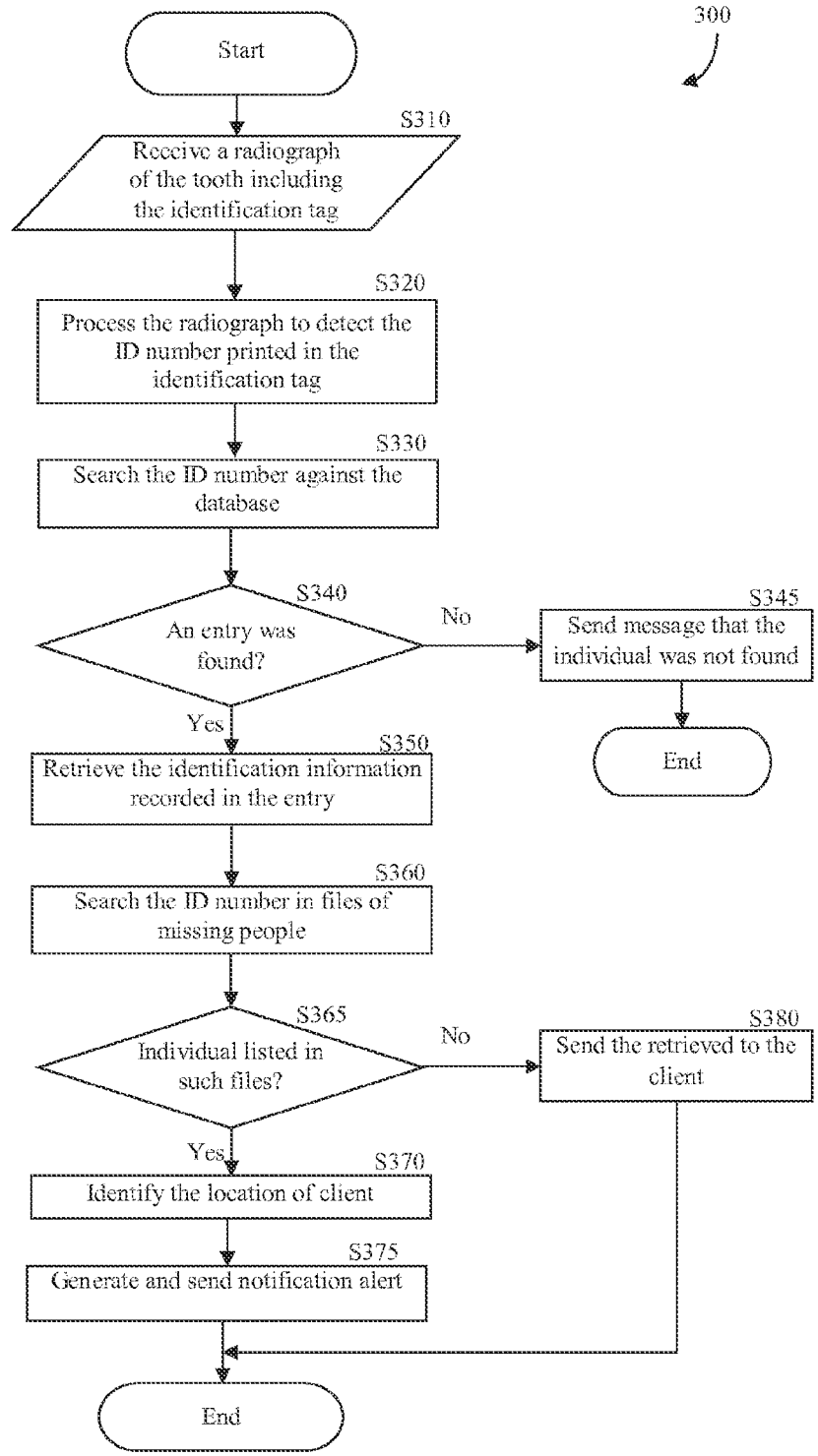
FIG. 3 is a flowchart of a method for dental-based identification of an individual according to one embodiment.

FIG. 3 shows an exemplary and non-limiting flowchart illustrating a method for identification of individuals using a dental-based identification tag according to one embodiment. The dental-based identification tag is bonded to a tooth of an individual and includes a unique ID number printed using radio-opaque ink. Thus, the printed ID number can be visible when an X-ray image of the jaw bone is taken. When the dental-based identification tag is bonded to the tooth, the tag is registered in the central database (e.g., database 244) together with the identification information of the individual. As part of the registration process, an X-ray image of the tag (prior to bonding) is taken to confirm the ID number printed therein. Further, an X-ray of the tooth with the identification tag can also be taken and recorded in the central database to be later used as a reference. The identification information recorded together with the ID number included in the tag includes, but is not limited to, name, age, gender, medical information, eye color, height, contact information in case of emergency, and so on.

At S310, a radiograph of at least the tooth including the dental-based identification tag is uploaded to the identification server. The radiograph can be uploaded from a client device that communicates with the identification server over a network. The radiograph may be, for example, of a patient visiting a dentist or of skeletal remains.

At S320, the uploaded radiograph is processed to detect the ID number printed in the tag. As the ID number is printed using radio-opaque ink, the ID number is visible in the radiograph, thus can be detected using image processing techniques. At S330, the detected ID number is searched against ID numbers of all identification tags recorded in the central database. At S340, a check is made to determine if an entry corresponding to the detected ID number has been found in the database, and if so, execution continues with S350; otherwise, at S345, a message is generated indicating the ID number was not found.

At S350, the identification information of the individual as recorded in the entry corresponding to the detected ID number is retrieved from the central database. Optionally, at S360, the identification information or the detected ID number are searched in one or more databases that include files of missing people, abducted children, open murder cases, accident cases, and the like.

At S365, a check is made to determine if the individual is listed in one of such files, and if so, at S370, the location of the client that uploaded the radiograph is detected, for example, based on its IP address. Then, at S375, a notification alert including the retrieved identification and the location is generated and sent to enforcement authorities, the client, and/or to the recorded contact information. If S365 results in a negative answer, at S380, the retrieved identification information is sent back to the client who uploaded the radiograph.

The foregoing detailed description has set forth a few of the many forms that the invention can take. It is intended that the foregoing detailed description be understood as an illustration of selected forms that the invention can take and not as a limitation to the definition of the invention.

Most preferably, the various embodiments of the invention can be implemented as any combination of hardware, firmware, and software. Moreover, the software is preferably implemented as an application program tangibly embodied on a program storage unit or computer readable medium. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

What is claimed is:

1. A dental-based identification system for identification of individuals, comprising:
    a database configured to maintain a record of each individual registered in the system, wherein each record includes at least an identification (ID) number included in a dental-based identification tag and identification information of the individual, wherein the ID number uniquely identifies the individual; and
    an identification server configured to receive a radiograph of at least one tooth to which the dental-based identification tag is bonded, to detect the ID number included in the dental-based identification tag, and to search a recording associated with the detected ID number, wherein the identification server is further configured to generate and send a message upon identification of the individual,
    wherein the ID number is printed on the dental-based identification tag using radio-opaque ink.

2. The system of claim 1, wherein the identification server is further configured to search if the detected ID number is found in files of at least one of: missing people, abducted children, open murder cases, and open accident cases.

3. The system of claim 2, wherein the identification server is further configured to identify a location from which the radiograph was sent.

4. The system of claim 3, wherein the identification server is further configured to generate a notification alert if the detected ID number is found in the files, wherein the notification alert includes identification information of the individual associated with the detected ID number and the location.

5. The system of claim 4, wherein the notification alert is sent to at least one of: an authorized user of the system and an enforcement authority.

6. The system of claim 1, wherein the dental-based identification tag is made of a clear plastic material.

7. The system of claim 1, wherein the dental-based identification tag is bonded to the tooth using a bonding agent.

8. The system of claim 1, wherein the dental-based identification tag is installed in a dental crown being bonded to the tooth using a dental cement.

9. The dental-based identification system of claim 1 wherein the ID number is printed on an interior surface of the dental-based identification tag and the interior surface is bonded to the at least one tooth.

10. A method dental-based identification system for identification of individuals, comprising:
- receiving a radiograph of at least one tooth to which a dental-based identification tag is bonded;
- detecting an identification (ID) number included in the dental-based identification tag, wherein the ID number uniquely identifies the individual;
- searching a database to find a record associated with the detected ID number, wherein the database maintains a record of each registered individual, each record includes at least an ID number and identification information of the individual; and
- generating a message upon identification of the individual, wherein the ID number is printed on the dental-based identification tag using radio-opaque ink.

11. The method of claim 10, further comprises recording the individual in the database by:
- taking an X-ray image of the dental-based identification tag to confirm the ID number;
- taking an X-ray image of the at least one tooth including the dental-based identification tag;
- creating a record in the database; and
- recording the ID number, the X-ray image of the at least one tooth, and identification of the individual in the record.

12. The method of claim 10, further comprising:
- searching if the detected ID number is found in files of at least one of: missing people, abducted children, open murder cases, and open accident cases.

13. The method of claim 12, further comprising:
- identifying a location from which the radiograph is sent.

14. The method of claim 13, further comprising:
- generating a notification alert if the detected ID number is found in the files, wherein the notification alert includes identification information of the individual associated with the detected ID number and the location.

15. The method of claim 14, wherein the notification alert is sent to at least one of an authorized user of the system and an enforcement authority.

16. A non-transitory computer readable medium having stored thereon instructions for causing one or more processing units to execute the method according to claim 10.

17. A dental-based identification tag, comprising:
- a sticker bonded to a tooth of person using a bonding agent, wherein an identification number is printed on the sticker using radio-opaque ink, wherein the ID number uniquely identifies the individual.

18. The dental-based identification tag of claim 17, wherein the dental-based identification tag is installed in a dental crown being bonded to the tooth using dental cement.

19. The dental-based identification tag of claim 17 wherein the ID number is printed on an interior surface of the dental-based identification tag.

20. The dental-based identification tag of claim 17 wherein the ID number is printed in a color identical to that of the sticker.

* * * * *